(12) United States Patent
Hancock et al.

(10) Patent No.: US 11,376,068 B2
(45) Date of Patent: Jul. 5, 2022

(54) ELECTROSURGICAL INSTRUMENT

(71) Applicant: CREO MEDICAL LIMITED, Monmouthshire (GB)

(72) Inventors: Christopher Paul Hancock, Bath and North East Somerset (GB); Patrick Burn, Monmouthshire (GB); Malcolm White, Monmouthshire (GB)

(73) Assignee: CREO MEDICAL LIMITED, Chepstow (GB)

( * ) Notice: Subject to any disclaimer, the term of this patent is extended or adjusted under 35 U.S.C. 154(b) by 636 days.

(21) Appl. No.: 16/328,682

(22) PCT Filed: Mar. 29, 2018

(86) PCT No.: PCT/EP2018/058092
§ 371 (c)(1),
(2) Date: Feb. 26, 2019

(87) PCT Pub. No.: WO2018/178244
PCT Pub. Date: Oct. 4, 2018

(65) Prior Publication Data
US 2019/0201095 A1 Jul. 4, 2019

(30) Foreign Application Priority Data

Mar. 30, 2017 (GB) .................................... 1705172

(51) Int. Cl.
*A61B 18/18* (2006.01)
*A61B 18/00* (2006.01)

(52) U.S. Cl.
CPC ..................... *A61B 18/1815* (2013.01); *A61B 2018/00541* (2013.01); *A61B 2018/00577* (2013.01);
(Continued)

(58) Field of Classification Search
CPC ...... A61B 18/1815; A61B 2018/00732; A61B 2018/1823; A61B 2018/00577;
(Continued)

(56) References Cited

U.S. PATENT DOCUMENTS

2008/0140062 A1* 6/2008 Cronin ............... A61B 18/1815
606/33
2011/0208177 A1* 8/2011 Brannan ................ A61B 18/08
606/33

(Continued)

OTHER PUBLICATIONS

British Search Report of related Britsh Application: No. GB1705172.3 dated Aug. 31, 2017.
(Continued)

*Primary Examiner* — Michael F Peffley
(74) *Attorney, Agent, or Firm* — ArentFox Schiff LLP

(57) ABSTRACT

An electrosurgical instrument with a radiating tip portion having a relative permeability and/or relative permittivity that is selected to provide an electrical length for the radiating tip portion that enables effective delivery into biological tissue of microwave EM energy supplied thereto, at two or more frequencies of choice. The instrument has a radiating tip portion disposed to receive microwave EM energy from a coaxial cable, the radiating tip portion having a first effective relative permeability at a first frequency and a second effective relative permeability at a second frequency.

9 Claims, 2 Drawing Sheets

(52) U.S. Cl.
CPC ............... *A61B 2018/00642* (2013.01); *A61B 2018/00732* (2013.01); *A61B 2018/00785* (2013.01); *A61B 2018/1823* (2013.01); *A61B 2018/1861* (2013.01); *A61B 2018/1876* (2013.01)

(58) Field of Classification Search
CPC .... A61B 2018/1861; A61B 2018/1876; A61B 2017/00876
See application file for complete search history.

(56) References Cited

U.S. PATENT DOCUMENTS

| | | | |
|---|---|---|---|
| 2013/0292602 A1 | 11/2013 | Hill | |
| 2014/0378958 A1* | 12/2014 | Leussler | A61B 18/18 606/33 |
| 2017/0056106 A1* | 3/2017 | McErlean | A61B 18/1815 |
| 2018/0050218 A1* | 2/2018 | Copty | A61N 5/025 |
| 2018/0085138 A1* | 3/2018 | Preiss | A61B 17/32056 |
| 2020/0054396 A1* | 2/2020 | Pfannenstiel | A61B 18/1815 |

OTHER PUBLICATIONS

Written Opinion and International Search Report of related International Application No. PCT/EP2018/058092 dated Jul. 19, 2018.

* cited by examiner

ELECTROSURGICAL INSTRUMENT

CROSS-REFERENCE TO RELATED APPLICATIONS

This application is a National Stage entry of International Application No.: PCT/EP2018/058092, filed Mar. 29, 2018, which claims priority to Great Britain Patent Application No. 1705172.3, filed Mar. 30, 2017. The disclosures of the priority applications are hereby incorporated in their entirety by reference.

TECHNICAL FIELD

The present application relates to an electrosurgical instrument for delivering electromagnetic (EM) energy into biological tissue at multiple frequencies.

BACKGROUND TO THE INVENTION

Electrosurgical instruments and apparatus for supplying EM energy to body tissue are known.

Typically, apparatus for delivering EM energy to body tissue comprises a generator comprising a source of EM energy, and an electrosurgical instrument connected to the generator, for delivering the energy to tissue.

EM energy, and in particular microwave and radio-frequency (RF) energy, have been found to be useful in electrosurgical operations, for their ability to cut, coagulate, and ablate body tissue.

Furthermore, it is known to use microwave emitting probes to treat various conditions in the lungs. For example, microwave radiation can be used to treat asthma and ablate tumours or lesions in the lungs.

SUMMARY OF THE INVENTION

Different frequencies of microwave EM energy penetrate into biological tissue to different depths. Moreover, the application of higher frequencies of EM energy to biological tissue generally results in faster, more localised heating than lower frequencies. In effect, there is a trade-off between depth/volume of treatment (improved at low microwave frequencies) and speed of treatment (improved at high microwave frequencies).

The normal mechanism by which energy is transferred into biological tissue at microwave frequencies is dielectric heating, where the microwave EM energy drives molecular oscillations in the tissue. However, biological tissue adjacent to the dielectric heating zone also typically experiences a rise in temperature. The mechanism for this is conduction, i.e. heat energy dissipating outwards from the dielectric heating zone. The inventors have observed that a combination of these two heating mechanisms at two or more microwave frequencies can enable microwave EM energy to create a rapid rise in temperature in a larger treatment zone than is typically associated with single frequencies of microwave energy. Moreover, heating can be achieved in a shorter time frame than is possible if lower frequency (i.e. non-microwave) EM energy is used.

The inventors have also found that the use of two or more frequencies enables EM energy delivered by an electrosurgical instrument to be adapted to reflect changes in physical and dielectric properties of biological tissue caused by heating. In particular, changes in dielectric properties can affect a relative impedance match between an electrosurgical instrument and tissue into which it is inserted. They have found that the efficiency of energy delivery to biological tissue may be maximised by provided an initial treatment period at a higher microwave frequency followed by a subsequent treatment period at a lower microwave frequency.

By providing an instrument capable of delivering energy to tissue at two or more microwave frequencies, the inventors have been able to heat large volumes of tissue comparatively quickly.

At its most general, the present invention provides an electrosurgical instrument with a radiating tip portion having a relative permeability and/or relative permittivity that is selected to provide an electrical length for the radiating tip portion that enables effective delivery into biological tissue of microwave EM energy supplied thereto, at two or more frequencies of choice.

References herein to relative permeability mean relative magnetic permeability ($\mu_r$), i.e. the ratio of the magnetic permeability of the medium in question ($\mu$), to the magnetic permeability of free space/vacuum ($\mu$). Hence, relative permeability is a dimensionless measure of magnetic permeability relative to free space.

References herein to relative permittivity mean relative electric permittivity ($\varepsilon_r$), i.e. a ratio of the electric permittivity of the medium in question ($\varepsilon$), to the electric permittivity of free space ($\varepsilon$). Hence, relative permittivity is a dimensionless measure of electric permittivity relative to free space.

References herein to electrical length means the length of the radiating tip 'seen' by the EM energy, i.e. the effective length of the radiating tip in which the EM energy oscillates/resonates.

In a first aspect, the present invention provides an electrosurgical instrument for delivering microwave electromagnetic (EM) energy into biological tissue, the instrument comprising: a coaxial cable for conveying microwave EM energy at a first frequency and a second frequency, the second frequency being higher than the first frequency; and a radiating tip portion disposed at a distal end of the coaxial cable to receive microwave EM energy from the coaxial cable, the radiating tip portion having a first effective relative permeability at the first frequency and a second effective relative permeability at the second frequency, wherein the first effective relative permeability and the second effective relative permeability are selected to cause an electrical length of the radiating tip portion to support resonance and the first frequency and the second frequency respectively.

The radiating tip portion may include a magnetically-sensitive material, e.g. a ferromagnetic material, whose properties are selected to cause the value of the effective relative permeability to have different values at the first frequency and the second frequency. In particular, it is known for ferromagnetic materials to exhibit a significant variation in relative permeability with frequency across the microwave range (e.g. in the range 200 MHz to 2 GHz). Examples are disclosed in US 2013/0292602 A1. Normally these variations are undesirable, and therefore lie outside the intended operating frequencies of such materials. However, in the present invention, this variation is used to enable the same physical structure to resonate at different microwave frequencies.

An external biasing magnetic field may be applied to the instrument to cause the magnetically-sensitive material provide a desired relative permeability value. The magnetic field may be provided by a inductive coil within the radiating tip portion, or may be applied from a separate source outside the instrument. In some examples, the magnetically sensitive material may be a self-magnetizing ferrite.

In this specification "microwave" may be used broadly to indicate a frequency range of 400 MHz to 100 GHz, but preferably the range 400 MHz to 10 GHz. Specific frequencies that have been considered are: 433 MHz, 915 MHz, 2.45 GHz, 3.3 GHz, 5.8 GHz, 10 GHz, 14.5 GHz and 24 GHz.

References herein to a "conductor" or "conductive" material herein are to be interpreted as meaning electrically conductive unless the context makes clear that another meaning is intended.

References herein to an "axial" direction refers to a direction parallel to the longitudinal axis of the coaxial cable.

References herein to the distal end of the coaxial cable (and any other constituent part of the instrument) means an end that is distal from a notional generator supplying the EM energy to the coaxial cable, i.e. distal from an end of the coaxial cable that is configured to receive EM energy from a generator.

When resonance of EM energy is supported in the radiating tip portion of an electrosurgical instrument, more energy is stored in the radiating tip portion, the reflection of energy back down the coaxial cable (i.e. away from a treatment region into which the radiating tip portion is inserted) is reduced, and more of the energy is delivered to body tissue surrounding the radiating tip portion. In other words, effective delivery of energy into body tissue is realised when resonance is supported in the radiating tip portion.

For the purpose of the present application, resonance is defined as a situation in which the power reflected at the radiating tip portion (i.e. reflected power $S_{1,1}$ as measured at a proximal end of the coaxial cable) is −10 dB, or better. Preferably, the power reflected at the radiating tip portion is −12 dB, or better. More preferably, the power reflected at the radiating tip portion is −15 dB, or better.

Hence, by supporting resonance at multiple microwave frequencies, energy is effectively delivered to tissue, and a large volume of tissue can be heated comparatively quickly.

Tumours in the lungs can grow to be up to a few centimetres in diameter. Given that sub-GHz frequencies of microwave EM energy (i.e. EM energy with frequencies from 300 MHz to 1 GHz) penetrate deepest into tissue, one approach for treating tumours of this size is to provide an instrument with a radiating tip portion capable of supporting resonance at two or more frequencies including a frequency in this range. Using such an instrument, microwave energy with large penetration depths can be used to effectively heat and ablate tumours of this size. However, as will become clear below, a difficulty with supporting resonance of microwave energy at sub-GHz frequencies, is that the radiating tip portion must necessarily have a larger electrical length in the axial direction. In conventional arrangements, this requirement typically led to physically long instruments, which can be difficult to manoeuvre in the body, and can make it difficult target heating effects at specific regions of tissue, e.g. at individual tumours in the lung.

In particular, if the radiating tip portion becomes too long, maneuvering it in percutaneous applications becomes very challenging, and maneuvering it in non-percutaneous applications (i.e. where a lung tumour is to be accessed via a natural airway using a bronchoscope) becomes impossible.

Resonance occurs when the electrical length of a cavity in which a wave oscillates is approximately equal to an integer multiple of one half of the wavelength or an odd integer multiple of a quarter-wavelength of the wave that propagates in the cavity, thereby enabling a standing wave to exist with a displacement node or maximum at each end of the cavity. For the radiating tip portion of an instrument to support resonance, it must therefore have an electrical length that substantially satisfies:

$$L = \frac{n\lambda}{2} \text{ or } L = \frac{n\lambda}{2} - \frac{\lambda}{4}$$

where n is a positive integer, and λ is a wavelength of microwave EM energy that propagates in the radiating tip portion at one of the two of more frequencies of microwave EM energy. When the above equation is satisfied, a displacement node is established at each end of the cavity, and so a (resonant) standing wave is established. In the present invention, the radiating tip portion can be considered as a cavity in which the EM energy oscillates, and so resonance will be observed when the axial length of the radiating tip portion approximately satisfies the above equation.

In practice, the length of the radiating tip portion may have a length that differs from the length defined in the equation above by up to 10%. Preferably, the length only differs from the length defined above by up to 5%.

By factoring in the relationship between wavelength λ, and frequency (f):

$$\lambda = \frac{c_0}{f} \frac{1}{\sqrt{\mu_r \varepsilon_r}}$$

where c is the speed of light in vacuum, $\mu_r$ is relative permeability, and $\varepsilon_r$ is relative permittivity, we see that the length L of the radiating tip portion must substantially satisfy:

$$L = \frac{nc_0}{2f} \frac{1}{\sqrt{\mu_r \varepsilon_r}} \text{ or } \frac{2n-1}{4} \frac{c_0}{f} \frac{1}{\sqrt{\mu_r \varepsilon_r}}$$

For dielectric materials that are commonly used for the radiating tip portion of medical instruments, relative permeability $\mu_r$ may be substantially constant at the relevant treatment frequency.

By utilising knowledge of how the relative permeability of a material in the radiating tip portion varies with frequency, the present invention provides an instrument with a radiating tip that has an effective relative permeability that enables the radiating tip portion to have different electrical lengths at different frequencies. Suitable selection of the material can ensure that the radiating tip portion is a resonant structure at different frequencies. Resonance at lower (e.g. sub-GHz) frequencies can be supported with a physically shorter radiating tip portion by including such a magnetic material. Low (e.g. sub-GHz) frequency EM energy can therefore be effectively delivered to body tissue while maintaining maneuverability of the radiating tip portion in the body, and enabling specific regions of tissue to be targeted.

The principle behind the invention is that resonance can be achieved with same electrical length at (i) the first frequency f and first effective relative permeability $\mu_r$, and (ii) the second frequency f and second effective relative permeability $\mu_r$, e.g. as follows $$\frac{n_1 c_0}{2 f_1} \frac{1}{\sqrt{\mu_{r1} \varepsilon_r}} = \frac{n_2 c_0}{2 f_2} \frac{1}{\sqrt{\mu_{r2} \varepsilon_r}}$$

Assuming $\varepsilon_r$ does not vary between the frequencies, this expression simplifies to:

$$\frac{\mu_{r1}}{\mu_{r2}} = \left(\frac{n_1 f_2}{n_2 f_1}\right)^2$$

In one example, the first effective relative permeability may be equal to or greater than 5 for a first frequency equal to of less than 500 MHz (e.g. 433 MHz). The first effective relative permeability may be equal to or greater than 10. It may be 20 or more at frequencies of 500 MHz or less. The second effective relative permeability may be less than 5 for a second frequency greater than 500 MHz (e.g. 915 MHz, or 2.45 GHz). The second effective relative permeability may be equal to or less than 2. It may be equal to or less than 1.5.

In some embodiments, the frequency-dependence of the relative permeability is selected so that the same order resonances (i.e. resonances for which the corresponding standing wave has the same value of n) are realized at two frequencies of EM energy. For example, as the skilled person will understand, by providing a radiating tip portion that supports resonance of EM energy at 1 GHz, and for which the relative permeability of the radiating tip portion at 500 MHz is four times its relative permeability at 1 GHz, a resonance of the same order will also be supported in the radiating tip portion at 500 MHz (assuming a negligible variation in relative permittivity $\varepsilon_r$ of the radiating tip portion).

The coaxial cable may comprise an inner conductor, an outer conductor, and a first dielectric material separating the inner conductor and the outer conductor. The radiating tip portion may comprise a second dielectric material different from the first dielectric material of the coaxial cable.

The second dielectric material may have a lower impedance than the first dielectric material at each of the two or more frequencies of microwave EM energy. Moreover, the second dielectric material may have an impedance that lies between the impedance of the cable (typically 50Ω), and an impedance of the tissue into which the tip is inserted (typically much lower than 50Ω for body tissue). At certain lengths, the radiating tip portion may then work as an impedance transformer, as well as supporting resonance, in order to further prevent reflection from the radiating tip portion, and hence further promote delivery of energy into tissue.

In another aspect of the invention, the same effect can be achieved through variation in the effective relative permittivity of the radiating tip section. According to this aspect, there may be provided an electrosurgical instrument for delivering microwave electromagnetic (EM) energy into biological tissue, the instrument comprising: a coaxial cable for conveying microwave EM energy at a first frequency and a second frequency, the second frequency being higher than the first frequency; and a radiating tip portion disposed at a distal end of the coaxial cable to receive microwave EM energy from the coaxial cable, the radiating tip portion having a first effective relative permittivity at the first frequency and a second effective relative permittivity at the second frequency, wherein the first effective relative permittivity and the second effective relative permittivity are selected to cause an electrical length of the radiating tip portion to support resonance and the first frequency and the second frequency respectively. In other examples a combination of variation in relative permeability and relative permittivity may be used to provide the advantages of the invention.

As with relative permeability, the relative permittivity of the radiating tip portion may be selected to help reduce the length of the radiating top portion.

The relative permittivity may be 5 or more at each of the two or more frequencies. Preferably, the relative permittivity is 10 or more at each of the two or more frequencies. More preferably, the relative permittivity is 20 or more at each of the two or more frequencies. For example, the second dielectric material may be Eccostock® HiK500F, which has a relative permittivity of up to 30 at microwave frequencies.

One of the two or more frequencies may be 800 MHz or less. Preferably, one of the two or more frequencies may be 500 MHz or less. For example, the two or more frequencies may include at least one of: 433 MHz and 915 MHz. These frequencies of EM energy are known to produce particularly desirable heating effects, especially for ablating tumours.

In order to further benefit from the fast tissue heating effects provided by high microwave frequencies (in addition to the deep tissue heating provided by sub-GHz frequencies), the two or more frequencies may further include a frequency of 1 GHz or more. Preferably, the two or more frequencies further include one or more of: 2.45 GHz, 5.8 GHz, and 14.5 GHz. EM energy at these frequencies is known to produce particularly desirable heating effects, especially for ablating tumours.

Preferably, the radiating tip portion of the present invention supports resonance over the largest possible range of frequencies, in order to maximise penetration depth, and minimise treatment time. It has been found that by designing the radiating tip portion to support resonances at two or more frequencies ranging from 500 MHz or lower, to 1 GHz or higher, particularly fast treatment of large tumours, e.g. tumours up to a few cm in diameter, can be achieved.

The inventors have also found that the frequencies mentioned above can be combined to provide heating effects that are effective in the treatment of hemorrhoids and/or fistulas (in addition to tumours), and so it is envisioned that the present invention can further be used to treat hemorrhoids and fistulas, which can also grow to large sizes.

In some embodiments, the two or more frequencies at which resonance is supported may be dynamically adjustable by a control of the relative permeability of the radiating tip portion.

The relative permeability of the radiating tip portion may be controllable by a magnetization (and/or demagnetization) of the magnetic material. In particular, by changing the magnetization of the magnetic material (and hence the ratio B/H), relative permeability is changed:

$$\frac{B}{H} = \mu_0 \mu_r$$

where B is magnetic flux density, and H is magnetic field strength.

The magnetic material may be magnetized (and/or demagnetized) by an electromagnetic coil/solenoid at the radiating tip portion.

The radiating tip portion may comprise an elongate probe extending distally away from the coaxial cable, the elongate probe having a cylindrical shape with a diameter equal to or less than a diameter of the coaxial cable.

The outer diameter of the radiating tip portion may be substantially equal to the outer diameter of the coaxial cable.

The distal end of the radiating tip portion may be tapered to a point, so as to assist with percutaneous access to body tissue. Moreover, it may taper to a sharp point. Having a sharp/tapered end further helps with percutaneous insertion into the body.

Alternatively, the coaxial cable and radiating tip portion may be dimensioned so as to enable non-percutaneous access to body tissue, e.g. through a natural orifice/passage in the body of a patient. In embodiments in which the instrument is used non-percutaneously, the distal end of the radiating tip portion may be rounded, i.e. to prevent piercing an airway or other natural passageway in the body down which the instrument is to be passed.

The coaxial cable and radiating tip portion may be configured to be insertable down an instrument channel of a bronchoscope or endoscope. In particular, the coaxial cable will preferably be flexible in such embodiments, to assist with insertion e.g. into an airway.

The outer diameter of the radiating tip portion may be substantially equal to the outer diameter of the coaxial cable.

In some embodiments, the coaxial cable may have a hollow lumen passing through it, i.e. travelling parallel to the longitudinal axis of the coaxial cable. Such a hollow lumen may be used for delivering and/or removing fluid from a space surrounding the radiating tip portion.

In another aspect, there is provided an electrosurgical apparatus for delivering microwave electromagnetic (EM) energy into biological tissue, the apparatus comprising: a generator arranged to generate microwave EM energy at two or more different frequencies; and an electrosurgical instrument as set out above, wherein the coaxial cable has a proximal end connected to the generator to receive microwave EM energy therefrom.

The generator may comprise two or more separate microwave sources for generating microwave EM energy at a respective one of the two or more different frequencies. The generator may further comprise a signal combiner arranged to convey each signal to a common signal path that is connected to the coaxial cable. The signal combiner may be a multiplexer. The multiplexer may be operable as a switching unit for selecting a signal to be conveyed on the common signal path. Alternatively or additionally, the multiplexer may be operable to convey two or more of the signals on the common signal path in a simultaneous or quasi-simultaneous manner. For example, the multiplexer may be a time-domain multiplexer or a filter multiplexer.

The apparatus may include a surgical scoping device (e.g. bronchoscope or the like) having flexible instrument cord for non-invasive insertion to a treatment site, wherein the instrument cord includes an instrument channel, and wherein the electrosurgical instrument is dimensioned to be insertable within the instrument channel.

The generator may be operable to deliver microwave EM energy at the two or more different frequencies according to a predetermined energy delivery profile. The energy delivery profile may be selected according to a desired ablation depth, and/or a desired ablation zone shape. In some embodiments, the energy delivery profile may be selected based on a measured property of energy reflected from the radiating tip portion.

In one example, the generator may be operable under the predetermined energy delivery profile to: deliver a first signal during a first ablation period, the first signal comprises microwave EM energy having predominantly a first frequency; and deliver a second signal during a second ablation period, the second signal comprises microwave EM energy having predominantly a second frequency, which is less than the first frequency. The generator may switch or alternate between the three periods. In particular, the energy may be (rapidly) alternated between the three frequencies. Alternatively, the energy may be supplied at the three frequencies simultaneously. Where the generator switches between the three periods, the second period may follow the first period.

The first frequency may be either 2.45 GHz, 5.8 GHz, or 14.5 GHz. The second frequency may be either 433 MHz or 915 MHz.

The generator may further comprise additional ablation periods, e.g. a third ablation period for delivering a third signal with a frequency listed above and not used in the first or second period.

By supplying the EM energy using one of the delivery profiles outlined above, a large volume of tissue can be heated comparatively quickly.

The generator may be configured to deliver pulses of microwave energy in time with the breathing cycle of a patient. Hence, energy can be supplied when lungs are deflated, in order to provide a better relative impedance match between the coaxial cable, radiating tip portion, and tissue.

The generator may include a detector arranged to detect reflected power received back from the coaxial cable, and may be arranged to switch from one ablation period to the next ablation period based on the detected reflected power.

BRIEF DESCRIPTION OF THE DRAWINGS

Examples of the present invention are discussed in detail below with reference to the accompanying drawings, in which.

DETAILED DESCRIPTION; FURTHER OPTIONS AND PREFERENCES

Figure 1:
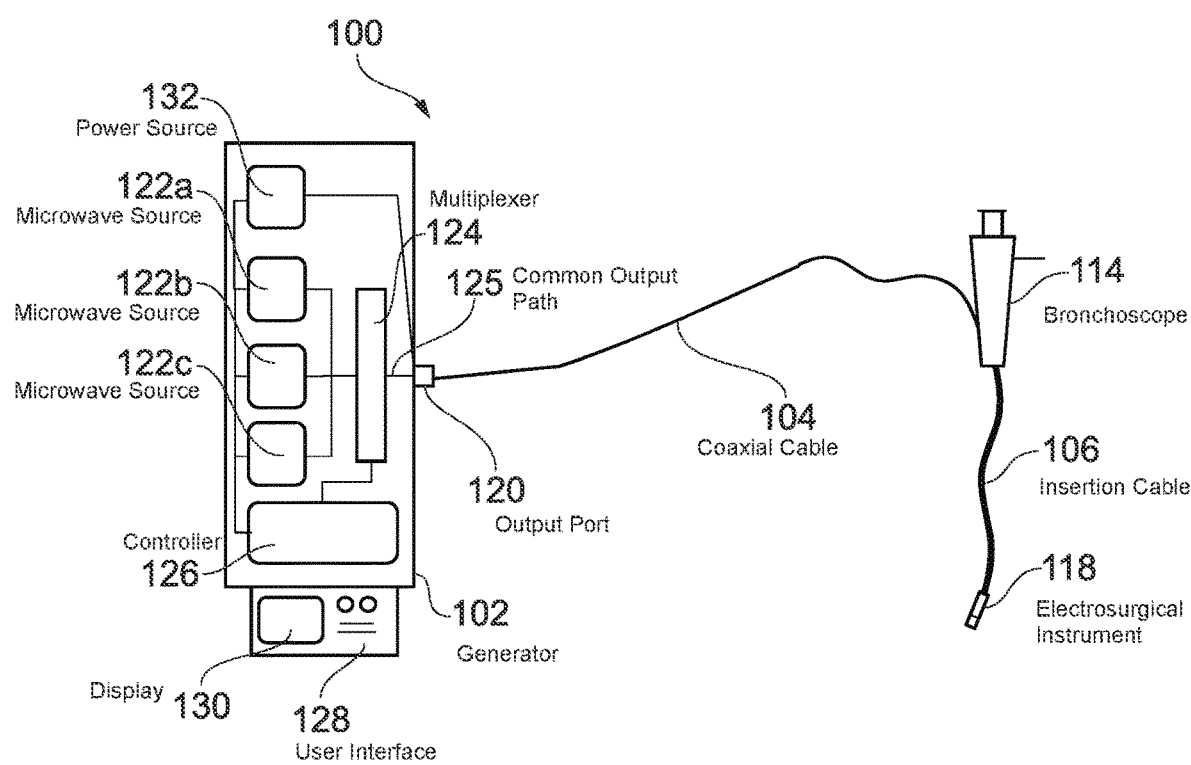
FIG. 1 is a schematic diagram of an electrosurgical apparatus that is an embodiment of the present invention.

FIG. 1 is a schematic diagram of an electrosurgical apparatus 100 that is an embodiment of the invention. The apparatus 100 is operable to selectively supply EM energy having a plurality of frequencies into biological tissue at a treatment site in a localised manner. The apparatus 100 comprises a generator 102 for generating EM energy having a plurality of frequencies. The generator 102 has an output port 120 to which is connected a coaxial cable 104. The coaxial cable 104 conveys the EM energy away from the generator 102 towards an electrosurgical instrument 118. In this embodiment, the coaxial cable 104 is inserted through an instrument channel within an insertion cable 106 of a bronchoscope 114. The insertion cable 106 is a flexible, steerable shaft capable of non-invasive insertion into a patient's lungs. This embodiment therefore enables a non-percutaneous insertion of the instrument 118. However, in other embodiments, the instrument 118 may have a distal tip configured for percutaneous insertion, i.e. for accessing lung tissue through an incision made in the body of a patient. In such an example, the instrument may be inserted directly into the tissue or via a suitable catheter.

The generator 102 comprises three separate microwave sources 122a, 122b, 122c. Each of the separate microwave sources 122a, 122b, 122c generates a signal having a different frequency. In this example, the frequencies are 433 MHz, 915 MHz and 5.8 GHz. Each of the separate microwave sources 122a, 122b, 122c may include a corresponding power amplifier for amplifying the respective signal to a power level suitable for use.

In some embodiments, the three sources may be integrated into a single component, e.g. a GaN power device. The use of a GaN power device, such as a GaN High Electron Mobility Transistor (HEMT)-based device, can enable the generator set-up to be miniaturised. On the other hand, the use of separate sources enables the cost of the generator to be kept to a minimum. Hence, the use of separate sources, or of a GaN power device, can be selected based on application.

The generator 102 includes a multiplexer 124 connected to receive an output signal from each of the separate microwave sources 122a, 122b, 122c. The multiplexer 124 operates to transfer the separate signals onto a common output path 125, which is connected to the output port 120. The multiplexer 124 may switch between the outputs of the separate microwave sources 122a, 122b, 122c, or may combine two or more of the outputs so that they are transmitted simultaneously. The multiplexer 124 may be operable as both a switch and a signal combiner.

The generator 102 includes a controller 126 operatively connected to the multiplexer 124 and each of the separate microwave sources 122a, 122b, 122c. The controller 126 can control operation of the generator 102 to output a desired signal. As discussed below, a desired output signal may have a predetermined format or profile, e.g. depending on the nature (shape or size) of the treatment site. The controller 126 may operate to deliver EM energy according to one or more delivery profiles. A user may be able to select a desired profile from a plurality of stored profiles, e.g. via a user interface 128 associated with the generator 102. For example, the generator may be configured in a similar manner to WO2012/076844, which discloses an electrosurgical apparatus in which RF and microwave energy are delivered to tissue down the same instrument, according to an energy delivery profile that can be set and automatically controlled based on feedback information.

The user interface 128 may include a display 130 for showing the selected profile and/or a stage or treatment or properties of tissue being treated.

Where the multiplexer 124 operates as a switch unit, generator 102 is capable of switching the energy supplied to the instrument between the three frequencies, according to a desired energy delivery profile. For example, the switch may first select the 2.45 GHz source, so that energy is delivered at 2.45 GHz, then switch to the 915 MHz source, so that energy is delivered at 915 MHz, and then switch to the 5.8 GHz source, so that energy is delivered at 5.8 GHz.

The multiplexer 124 may be a time-domain multiplexer. In this case, the multiplexer can rapidly alternate the energy supplied to the instrument between the three frequencies, according to a desired energy delivery profile. Alternatively, the multiplexer 124 may be a filter multiplexer, whereby it can supply the three frequencies to the instrument simultaneously, i.e. according to an energy delivery profile having a desired mixing ratio.

Hence, the energy delivery profile with which energy is delivered can be controlled by a combination of controlling an operational state of multiplexer 124 and the output of the separate microwave sources 122a, 122b, 122c.

In some embodiments, the generator 102 may include one or more reflected signal detectors arranged to measure reflected power received back from the radiating tip of the instrument 118. By comparing the reflected signal with a signal delivered from the generator to the radiating tip portion, the generator can determine dielectric properties of the material (e.g. biological tissue) in contact with the instrument 118. The controller may be able to adjust operation of the multiplexer 124 and the separate microwave sources 122a, 122b, 122c based on the detected reflected power. The generator 102 may thus dynamically control energy delivery based on detected dielectric properties of the tissue being treated.

In embodiments in which the instrument includes a solenoid for magnetizing and/or demagnetizing the radiating tip portion (see below), the controller may also be operatively connected to solenoid power source 132. Controller 126 can thereby control an output of the solenoid power source 132, thereby powering up the solenoid by a desired amount, i.e. so as to magnetize or demagnetize the magnetic material by a desired amount, and therefore change the resonant frequencies of the radiating tip portion by a desired amount.

Figure 2:
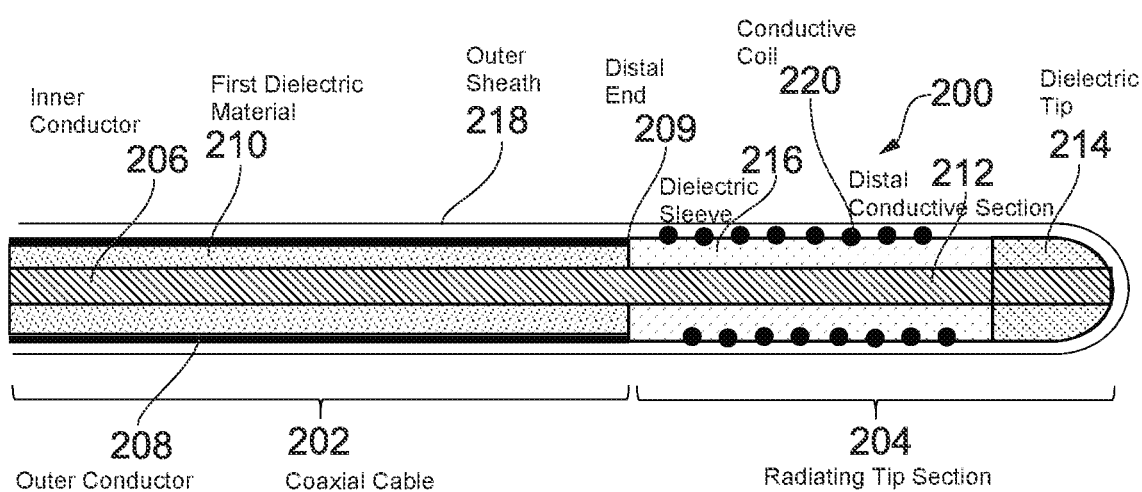
FIG. 2 is a schematic cross-sectional view through an electrosurgical instrument that is an embodiment of the invention.

FIG. 2 is a cross-sectional view of the distal end of an electrosurgical instrument 200 that is an embodiment of the invention. The electrosurgical instrument 200 comprises a coaxial cable 202 that is connected at its proximal end to a electrosurgical generator (not shown) in order to convey microwave energy. The coaxial cable 202 comprises an inner conductor 206, which is separated from an outer conductor 208 by a first dielectric material 210. The coaxial cable 202 is preferably a low loss for microwave energy. A choke (not shown) may be provided on the coaxial cable to inhibit back propagation of microwave energy reflected from the distal end and therefore limit backward heating along the device.

The coaxial cable 202 terminates at its distal end with a radiating tip section 204. In this embodiment, the radiating tip section 204 comprises a distal conductive section 212 of the inner conductor 206 that extends beyond a distal end 209 of the outer conductor 208. The distal conductive section 212 is surrounded at is distal end by a dielectric tip 214 formed from a second dielectric material, which is different from the first dielectric material 210. The length of the dielectric tip 214 is shorter than the length of the distal conductive section 212. An intermediate dielectric sleeve 216 surrounds the distal conductive section 212 between the distal end of the coaxial cable 202 and the proximal end of the dielectric tip 214. The intermediate dielectric sleeve 216 is formed from a third dielectric material, which is different from the first dielectric material 210 but which may be the same as the second dielectric material 214.

In this embodiment, the coaxial cable 202 and radiating tip section 204 have a outer sheath 218 formed over their outermost surfaces. The outer sheath 218 may be formed from a biocompatible material. The outer sheath 218 has a thickness that is small enough to ensure that it does not significantly interfere with the microwave energy radiated by the radiating tip section 204 (i.e. radiating pattern and return loss). In an embodiment, the sheath is made from PTFE, although other materials are also appropriate.

The dielectric tip 214 may be arranged to alter the shape of the radiated energy. The second dielectric material is selected to attenuate the radiation from the antenna, which results is a more spherical radiation pattern. To do this, the second dielectric material preferably has a large dielectric constant (relative permittivity $\varepsilon_r$). The dielectric constant of the second dielectric material is preferably chosen to enable the length of the dielectric tip 214 to be minimised whilst still constituting a non-negligible portion of a wavelength of the microwave energy when it propagates through the second dielectric material. It is desirable for the dielectric tip to be as short as possible in order to retain flexibility in the device, especially if the second dielectric material is rigid. In an embodiment, the dielectric tip may have a length equal to or less than 2 mm. The dielectric constant of the second dielectric material may be greater than 80, and is preferably 100 or more. The second dielectric material may be $TiO_2$ (titanium dioxide).

The wavelength of radiation in a material becomes shorter as the dielectric constant of the material increases. Therefore a dielectric tip 214 with a greater dielectric constant will have a greater effect on the radiation pattern. The larger the dielectric constant, the smaller the dielectric tip 214 can be while still having a substantial effect on the shape of the radiation pattern. Using a dielectric tip 214 with a large dielectric constant means that the antenna can be made small and so the instrument can remain flexible. For example the dielectric constant in $TiO_2$ is around 100. The wavelength of microwave radiation having a frequency of 5.8 GHz is about 6 mm in $TiO_2$ compared to around 36 mm in PTFE (which may be the material used for the first and/or third dielectric materials). A noticeable effect on the shape of the radiation pattern can be produced in this arrangement with a dielectric tip 214 of approximately 1 mm. As the dielectric tip 214 is short, it can be made from a rigid material whilst still maintaining flexibility of the antenna as a whole.

The dielectric tip 214 may have any suitable distal shape. In FIG. 2 it has a dome shape, but this is not necessarily essential. For example, it may be cylindrical, conical, etc. However, a smooth dome shape may be preferred because it increases the mobility of the antenna as it is maneuvered through small channels.

Meanwhile, the properties of the intermediate dielectric sleeve 216 are selectable to enable the radiating tip section 204 to efficiently deliver microwave EM energy at a plurality of (e.g. at two or more) frequencies. In particular, the intermediate dielectric sleeve 216 is made from a material chosen to be able to exhibit different value of relative permeability $\mu_r$ at a first frequency and a second frequency such that the electrical length of the radiating tip section 204 is a resonant length at both the first frequency and the second frequency.

In this example, the intermediate dielectric sleeve 216 is made from a ferrimagnetic material whose relative permeability $\mu_r$ is influenced by the presence of an external (biasing) magnetic field. In this example, the radiating tip section 204 includes a conductive coil 220 that is arranged to receive a current via a suitable feed (not shown) in the coaxial cable, e.g. from a solenoid in the generator. Current in the coil 220 induces a magnetic field across the intermediate dielectric sleeve 216. It is known that the relative permeability of ferrimagnetic material biased in this way depends on frequency. For higher frequencies, typically equal to or greater than 1 GHz, the relative permeability tends to unity. However, for lower frequencies, it can be higher, e.g. an order of magnitude higher in some cases.

With the arrangement show in FIG. 2, an effective relative permeability of the radiating tip section 204 can be controlled to have a first value $\mu_{r1}$ at a first frequency f and a second value $\mu_{r2}$ at a second frequency f such that the electrical length L of the radiating tip section 204 satisfies the relation:

$$L = \frac{n_1 c_0}{2 f_1} \frac{1}{\sqrt{\mu_{r1} \varepsilon_r}} = \frac{n_2 c_0}{2 f_2} \frac{1}{\sqrt{\mu_{r2} \varepsilon_r}}$$

Moreover, the biasing field from the coil 220 may be controlled to enable the first frequency f and the second frequency f to be varied.

The invention claimed is:

1. An electrosurgical instrument for delivering microwave electromagnetic (EM) energy into biological tissue, the instrument comprising:
    a coaxial cable for conveying microwave EM energy at a first frequency and a second frequency, the second frequency being higher than the first frequency; and
    a radiating tip portion disposed at a distal end of the coaxial cable to receive microwave EM energy from the coaxial cable, the radiating tip portion having a first effective relative permeability at the first frequency and a second effective relative permeability at the second frequency,
    wherein the first effective relative permeability and the second effective relative permeability are selected to cause an electrical length of the radiating tip portion to support resonance at the first frequency and the second frequency respectively.

2. The electrosurgical instrument according to claim 1, wherein the radiating tip portion comprises a second dielectric material different from a first dielectric material of the coaxial cable.

3. The electrosurgical instrument according to claim 2, wherein the second dielectric material is ferrimagnetic.

4. The electrosurgical instrument according to claim 2, wherein the radiating tip portion comprises a magnetizing element for applying a magnetic bias field to the second dielectric material.

5. The electrosurgical instrument according to claim 4, wherein the magnetizing element is an electromagnetic coil disposed around the second dielectric material.

6. The electrosurgical instrument according to claim 4, wherein the magnetizing element is controllable to adjust the magnetic bias field.

7. An electrosurgical instrument for delivering microwave electromagnetic (EM) energy into biological tissue, the instrument comprising:
    a coaxial cable for conveying microwave EM energy at a first frequency and a second frequency, the second frequency being higher than the first frequency; and
    a radiating tip portion disposed at a distal end of the coaxial cable to receive microwave EM energy from the coaxial cable, the radiating tip portion having a first effective relative permittivity at the first frequency and a second effective relative permittivity at the second frequency,
    wherein the first effective relative permittivity and the second effective relative permittivity are selected to cause an electrical length of the radiating tip portion to support resonance at the first frequency and the second frequency respectively.

8. An electrosurgical apparatus for delivering microwave electromagnetic (EM) energy into biological tissue, the apparatus comprising:
    an electrosurgical instrument according to claim 1; and
    a generator arranged to generate microwave EM energy at the first frequency and the second frequency, wherein the coaxial cable has a proximal end connected to the generator to receive microwave EM energy therefrom.

9. The electrosurgical apparatus of claim 8, including a surgical scoping device having a flexible instrument cord capable of non-invasive insertion to a treatment site, wherein the instrument cord includes an instrument channel, and wherein the electrosurgical instrument is dimensioned to be insertable within the instrument channel.

* * * * *